Figure 1:
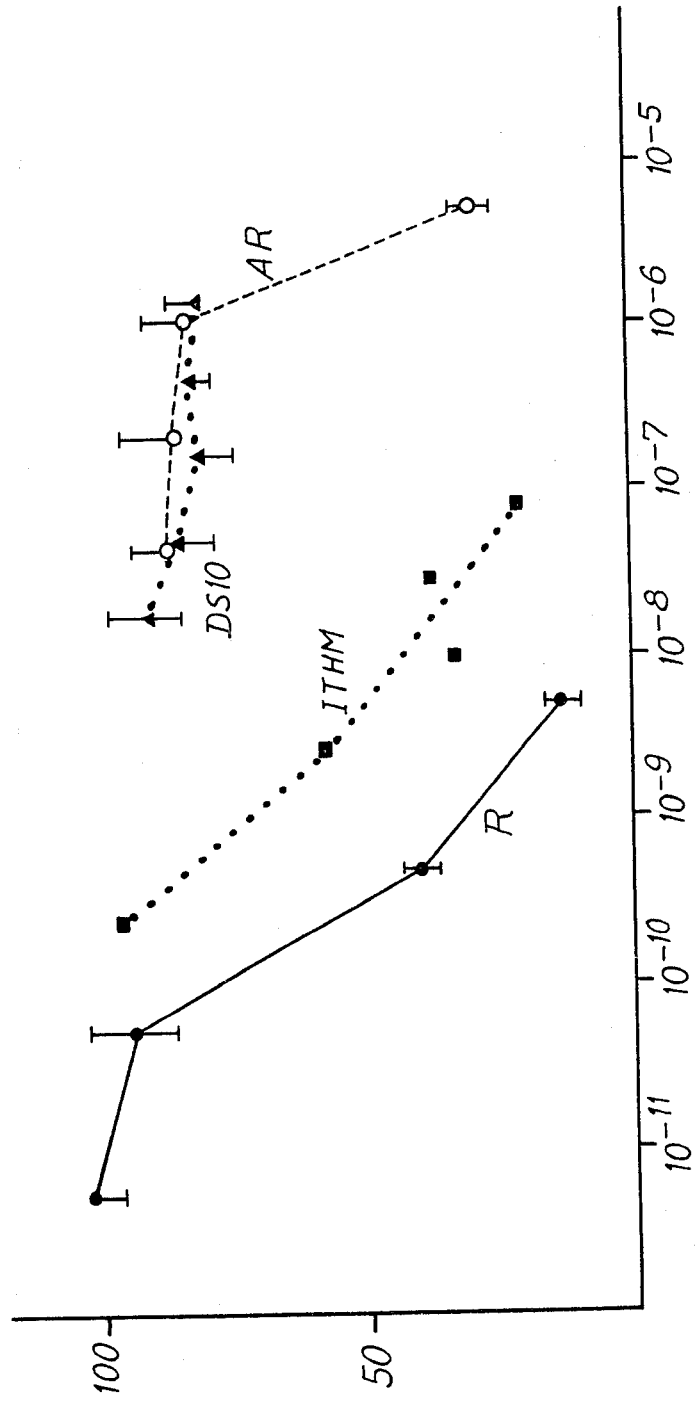

United States Patent [19]

Jansen et al.

[11] 4,414,148
[45] Nov. 8, 1983

[54] ANTI-CANCER DRUGS FOR THE TREATMENT OF MELANOMAS AND METHOD FOR PREPARING THEREOF

[75] Inventors: Franz K. Jansen, Castries; Pierre Gros, Montpellier, both of France

[73] Assignee: Sanofi, Paris, France

[21] Appl. No.: 368,434

[22] Filed: Apr. 14, 1982

[30] Foreign Application Priority Data

Apr. 15, 1981 [FR] France .................................. 81 07596

[51] Int. Cl.³ .......................... A61K 39/44; C07G 7/00
[52] U.S. Cl. .................................... 260/112 B; 424/85
[58] Field of Search ........................ 260/112 B; 424/85

[56] References Cited

U.S. PATENT DOCUMENTS 4,340,535 7/1982 Voisin et al. ............... 260/112 R X

FOREIGN PATENT DOCUMENTS 23401 2/1981 European Pat. Off. .

OTHER PUBLICATIONS

Proc. Nat. Acad. Sci. USA, 77(4), 2183–2187, (1980), Woodbury et al.
Chem. Abstracts, vol. 95, 1981, 35295p, Blythman et al.
Chem. Abstracts, vol. 94, 1981, 132084f, Pau et al.
Biol. Abstracts, vol. 71, 1981, 68145, Youle et al.
Biol. Abstracts, vol. 71, 1981, 68063, Yasuhiko et al.
Biol. Abstracts, vol. 71, 1981, 32655, Krolick et al.
Biol. Abstracts, vol. 71, 1981, 46810, Gilliland et al.
Biol. Abstracts, vol. 71, 1981, 46871, Jansen et al.
Biol. Abstracts, vol. 71, 1981, 68064, Miyazaki et al.

Primary Examiner—Howard E. Schain
Attorney, Agent, or Firm—Weingarten, Schurgin, Gagnebin & Hayes

[57] ABSTRACT

The present invention relates to drugs useful in particular for the treatment of melanomas, characterized in that they contain an active substance which is a molecule in which the chain A of ricin is associated, by a covalent bond of disulfide type, with a human antimelanoma antibody.

4 Claims, 2 Drawing Figures

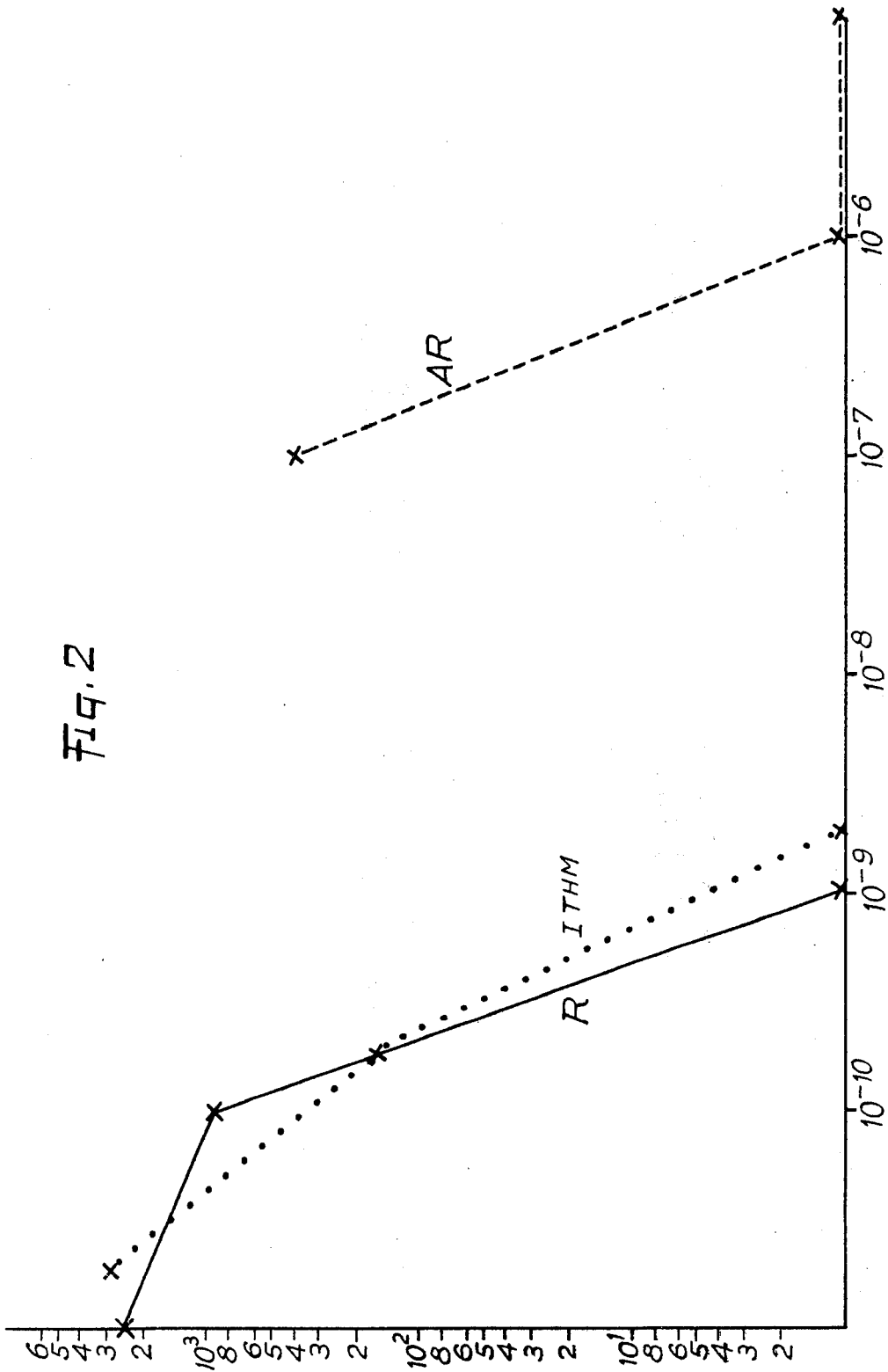

ANTI-CANCER DRUGS FOR THE TREATMENT OF MELANOMAS AND METHOD FOR PREPARING THEREOF

The present invention relates to anti-cancer drugs containing the chain A of ricin associated with an antimelanoma antibody and to a method for preparation thereof.

In earlier Applications Nos. 78 27838 of Sept. 28, 1978 and Addition No. 79 24655 of Oct. 3, 1979, Applicants have described the preparation of so-called conjugate anti-cancer products obtained by coupling by covalent bond of the chain A of ricin with a protein structure such as an antibody, an immunoglobulin or a fragment of immunoglobulin capable of selectively recognizing an antigen associated with the surface of the carrier cells which it is desired to reach, such as the cancerous cells. The main property of these conjugates is that they are cytotoxic agents specific of the target cells aimed at.

The use of antibodies directed against the antigens of differentiation of the cancerous cells had already enabled conjugates to be obtained presenting a noteworthy specificity vis-à-vis the target cells. The characterization of antigens associated with the cancerous cells and the obtaining of monoclonal antibodies directed against these antigens make it possible to envisage conjugates presenting an increased specificity vis-à-vis the carrier cells of these antigens.

It is an object of the present invention to produce, by way of drugs, so-called conjugate products obtained from the chain A of ricin and from a human antimelanoma monoclonal antibody.

Conjugates are understood to mean artificial mixed molecules in which the chain A of ricin is associated by a covalent bond of disulfide type with a human antimelanoma antibody capable of selectively recognizing an antigen associated with the cancerous cells.

The obtaining of the chain A of pure ricin has been described in Applicants' earlier Patents. The preparation of monoclonal antibodies directed against human melanomas has been mentioned in scientific literature [particular reference may be made to Proceedings of the National Academy of Sciences 77 (4), 2183–7, (1980)].

To produce the conjugates, the proteins to be coupled must each carry at least one atom of sulfur naturally adapted or artificially rendered adapted to create the desired disulfide bond.

The chain A of ricin naturally presents one atom of sulfur allowing the desired coupling. It is that of the thiol function of the residue of cysteine included in the chain A and which ensured the bond of this chain A with the chain B in the complete toxin.

The antimelanoma antibody comprises neither free thiol function nor other atoms of sulfur capable of being used for coupling. One or more atoms of sulfur should therefore be introduced artificially on the molecule of immunoglobulin, which atoms are capable of being subsequently engaged in the disulfide bond to be established with one or more molecules of chain A of ricin.

According to the invention, the preparation of the conjugate is effected by bringing together the chain A of ricin carrying its free SH group with the antibody in which the SH group has been artificially introduced in activated form and particularly in the form of a mixed disulfide with a suitable sulfured organic radical.

The preparation of the conjugate may be represented by the scheme:

RA—SH+AC—S—S—X→
RA—S—S—AC+XSH in which:

RA designates the chain A of ricin
AC designates the antibody
X designates the activator radical.

The antibody substituted by an atom of activated sulfur is obtained from the antibody itself, by substitution with the aid of a reagent itself carrier of an atom of activated sulfur according to the scheme:

AC+Y—R—S—S—X→AC—R—S—S—X in which:

AC designates the antibody
Y represents a function allowing the covalent fixation of the reagent on the protein
R designates a group which may simultaneously carry the substituents Y and —S—S—X.
X designates the activator radical.

The functional group Y is a functional capable of being bonded in covalent fashion with any one of the functions carried by the side chains of the aminoacids constituting the protein to be substituted. From these, the terminal amino functions of the lysyl radicals contained in the protein are particularly indicated. In this case, Y may represent, in particular:

- a carboxylic group which may be bonded to the amino functions of the protein in the presence of a coupling agent such as a carbodiimide and in particular a water-soluble derivative such as 1-ethyl 3-(3-diethylamino propyl)carbodiimide,
- a carboxylic acid chloride which is capable of reacting directly with the amino functions to acylate them,
- a so-called "activated" ester such as an ester of ortho- or para-, nitro- or dinitro-phenyl or an ester of N-hydroxysuccinimide which reacts directly with the amino functions to acylate them,
- an internal anhydride of a carboxylic diacid such as for example succinic anhydride which reacts spontaneously with the amine functions to create amine bonds,
- an imidoester group 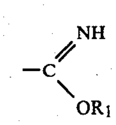 where $R_1$ is an alkyl group reacting with the amino groups of the protein according to the reaction:

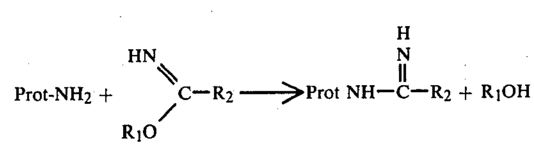

X designates a functional group capable of reacting with a free thiol radical. In particular, X may designate a 2-pyridyl or 4-pyridyl group possibly substituted by one or more alkyl, halogen, carboxylic radicals. X may also designate a phenyl group preferably substituted by one or more nitro- or carboxylic groups. X may also represent an alkoxycarbonyl group such as the methoxycarbonyl group.

The radical R designates any radical capable of simultaneously carrying the substituents Y and S—S—X. It must be selected so as not to comprise functions capable of interfering in the course of the subsequent reactions with the reagents used and the synthesized products. In particular, the group R may be a —$(CH_2)_n$ group with n between 1 and 10, or a group:

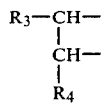

in which $R_4$ designates hydrogen or an alkyl group having from 1 to 8 carbon atoms and $R_3$ designates a substituent inert vis-à-vis the reagents used subsequently such as a carbamate group

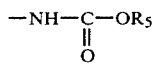

where $R_5$ designates a linear or branched alkyl group having from 1 to 5 atoms of carbon and particularly the tertiobutyl group.

The reaction of the compound Y—R—S—S—X with the immunoglobulin is effected in homogeneous liquid phase most often in water or a buffer solution. When the solubility of the reagents requires this, it is possible to add to the reaction medium up to 20% by volume of an organic solvent mixable in water such as an alcohol and particularly tertiary butanol.

The reaction is effected at ambient temperature for a period varying from a few hours to 24 hours, after which a dialysis makes it possible to eliminate the products of low molecular mass and in particular the excesses of reagents. This process allows introduction of a number of substituent groups per mole of protein of between 1 and 5 if the protein is an immunoglobulin of class G, between 1 and 15 if the protein is an immunoglobulin of class M.

By using such compounds, coupling with chain A of ricin is effected by bringing together the two proteins in aqueous solution at a temperature not exceeding 30° C. for a period of time varying from a few hours to one day. The solution obtained is dialysed to eliminate the products of low molecular mass, then the conjugate may be purified by various known methods.

The following examples enables the invention to be more readily understood without limiting the scope thereof.

EXAMPLE 1

Conjugate obtained from human antimelanoma antibody (antibody directed against the antigen P 97) substituted by an activated disulfide group and the chain A of ricin.

(a) Human antimelanoma antibody (anti P 97)

This antibody was obtained according to the method described in Proceedings of National Academy of Sciences 1980, 77 (4), 2183–7.

It undergoes ultimate purification by dialysis against PBS buffer (10 mM of phosphate, 140 mM of sodium chloride, pH:7.4).

(b) Chain A of ricin

The chain A of ricin was prepared and purified as indicated in Applicants' earlier Applications (Patent No. 78 27838 and Addition No. 79 24655).

(c) Activated human antimelanoma antibody

To 0.5 ml of a solution of 20 mg/ml of 3-(2-pyridyl disulfanyl)-propionic acid in tertiobutanol is added 0.2 ml of a solution of 60 mg/ml of 1-ethyl 3(3-dimethylamino-propyl)carbodiimide and is left for 3 minutes at ambient temperature.

30 μl of the solution thus obtained are added to 1.66 ml of a solution of antimelanoma antibody with 2.4 mg/ml in the PBS buffer. Incubation is allowed to continue for 20 hours at 30° C.

The solution is then continuously dialysed for 3 days against 21 liters of PBS buffer at 4° C. In this way, 4 mg of activated antibody are obtained, at a concentration of 2.3 mg/ml.

By spectrophotometric dosage at 343 nm of the pyridine 2-thione released by exchange with the reduced glutathion, it is observed that an antibody is obtained, carrying 2.6 activator groups per mole of antibody.

(d) Conjugate

To 1.3 ml of a solution of activated antibody in the PBS buffer (concentration 2.3 mg/ml, or 3 mg of activated antibody), is added 0.52 ml of a solution of chain A of ricin in the same buffer (concentration 5.8 mg/ml) and incubation is effected at 25° C. for 20 hours.

The reaction mixture is chromatographed on a Sephadex G 100 gel column. In each fraction, the concentration of antibodies is determined by spectrophotometry at 280 nm and that of the chain A by its inhibitory power of proteosynthesis measured on an acellular system. The identical fractions containing the conjugate are combined, and about 1 mg of the conjugate is thus obtained, at the concentration of 0.2 mg/ml.

The analytical determinations carried out show that the solution contains 50 μg/ml of biologically active chain A, or about 1.4 mole of chain A per mole of antibody.

A study made by cytofluorometry further demonstrated that the antimelanoma antibody used, the corresponding activated antibody and the conjugate of this antibody with the chain A of ricin present very similar fluoroescence histograms confirming that the antibody has not undergone any important alteration in the course of the activation and coupling reactions to which it was subjected and in particular that it remains capable, within the conjugate, of recognizing the antigen P 97 against which it is directed.

The conjugate according to the invention, obtained previously, has been studied as far as its biological properties and more especially its anti-cancer action are concerned.

(1) Inhibition of proteosynthesis

The fundamental biological property of the chain A of ricin is to inhibit the cellular proteosynthesis by alteration of the ribosomal sub-unit 60 S.

A cellular model has been used here. This test measures the effect of the substances studied on the incorporation of $^{14}C$-leucine in the cancerous cells in culture.

The cells used belong to the cellular issue M 1477 issuing from a human melanoma which carries the antigen P 97. These cells, after trypsination, are preincubated at least 24 hours in order to allow re-expression of the possibly altered surface antigens. After addition of the substance to be studied, a fresh incubation is effected. At the end of incubation, the rate of incorporation of $^{14}C$-leucine by the cells thus treated is measured.

This measurement is effected according to a technique adapted from the technique described in Journal of Biological Chemistry 1974, 249 (11), 3557-62 using the $^{14}C$-leucine tracer for determining the rate of proteosynthesis. The determination of the incorporated radioactivity is effected here on the entire cells isolated by filtration.

From these determinations, the effect/dose curves may be plotted, presenting on the x-axis the concentration of the substances studied and, on the y-axis, the incorporation of $^{14}C$-leucine expressed in percentage of the incorporation of the control cells in the absence of the substance to be studied.

For each substance studied, the concentration which inhibits 50% of the incorporation of $^{14}C$-leucine or "inhibitory concentration 50" (IC 50) may thus be determined.

The results obtained with the conjugate prepared in the preceding Example (ITHM) are shown in FIG. 1. The figure also shows the curves obtained respectively with ricin (R), the chain A of ricin (AR) and a ricin chain A-anti radical dinitrophenyl (DNP) antibody (DS 10) conjugate, which conjugate presents no affinity for the cells tested.

It may be observed from this figure that the conjugate studied (ITHM) presents a considerable cytoxic activity (IC 50–$5 \times 10^{-9}$ M), about 400 times greater than that of chain A of recin.

Furthermore, the anti-DNP (DS 10) conjugate has no effect on the cells M 1477 up to the highest concentration tested ($10^{-6}$M). On the contrary, this same conjugate DS 10 proves cytotoxic with an IC 50 close to $10^{-9}$M if it is brought in the presence of the same cells M 1477 previously rendered artificially carriers of DNP radicals. These two latter conclusions demonstrate the character specific of the cytotoxic activity of the conjugate ITHM.

(2) Inhibition of the formation of colonies

The melanoma cells M 1477 in culture are detached from their support by Versene solution (PBS buffer containing ethylene diamine tetracetic acid) or by trypsinisation. These cells are seeded at a rate of $2 \times 10^4$ cells per Petri dish of 5 cm diameter containing the following culture medium:

RPMI 1 6 4 0 (Mérieux) medium supplemented with glutamine 2 mM, sodium bicarbonate 2 g/l, 15% inactivated foetal serum of calf (Seromed) and antibiotics (penicillin, streptomycine and amphotericine B).

After 24 hours, the cells are treated with various concentrations of the conjugate to be studied.

By way of comparison, the same series of experiments is carried out with ricin, on the one hand, with the chain A of ricin, on the other hand, and finally with a conjugate non-specific of this cellular issue (conjugate chain A of ricin and an anti-DNP (DS 10) antibody).

After a further 24 hours, the culture medium is eliminated and replaced by the same fresh medium, having no cytotoxic substance.

10 to 15 days later, the number of colonies which have developed is determined after coloration with a violet crystal solution with the aid of an automatic colony counter (Artek 880 system).

This method allows detection of a quantity as little as 10 viable cells per dish, as was verified by using control cultures. It has also been demonstrated that the formation of colonies is strictly proportional to the initial concentration of the cells, at least within the limit of $10^1$ to $10^4$ cells per ml.

The results obtained are shown in FIG. 2 in which the number of colonies per dish have been plotted on the y-axis, and in logarithmic coordinates, and the concentration of the product on the x-axis. The tests were carried out for ricin (R), the chain A of ricin (AR) and the conjugate product according to the invention (ITHM).

The conjugate ITHM presents considerable activity since the last cell of melanoma is killed at a concentration of about $2 \times 10^{-9}$M of conjugate. This concentration is comparable to that of ricin ($1 \times 10^{-9}$M) whilst, for the chain A of ricin, $10^{-6}$M must be attained to obtain the same effect.

It may also be noted that the conjugate DS 10 has no activity up to $2 \times 10^{-8}$M, the highest concentration at which it was tested.

The conclusions of this experiment entirely confirm those of the proteosynthesis inhibition experiment.

The conjugates prepared according to the invention therefore present a considerable specificity of action vis-à-vis the cellular issues of human melanoma. They may therefore be used in human therapeutics in the treatment of melanomas and possibly other cancerous or non-cancerous affections sensitive to the antibody used.

These conjugates are in a form suitable for administration by the injectable route. They may be used either alone or associated with another treatment of the cancerous affection concerned and, in particular, associated with other immunodepressant drugs in order to delay and weaken the natural immunitary reaction of the patient vis-a-vis the protein foreign to his organism represented by the conjugate.

As it aims to eliminate all the cancerous cells, the treatment must be carried out with a sufficient dose of conjugate and the duration of treatment must be determined in each case as a function of the subject and the nature of the affection to be treated.

What is claimed is:

1. Drugs useful in particular for the treatment of melanomas, wherein they contain an active substance which is a molecule in which the chain A of ricin is associated, by a covalent bond of disulfide type, with the human antimelanoma antibody, Anti p. 97.

2. The drugs of claims 1, wherein they are in a form suitable for administration by the injectable route.

3. Method for preparing the active substance of the drug of claim 1, wherein the chain A of ricin-chain represented by the formula RASH-is reacted with a derivative of the antibody, Anti-p. 97, of formula AC—S—S—X in which X designates an activator radical, and AC designates Anti-p. 97, according to the equation:

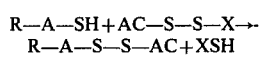

4. The process of claim 3, wherein the radical X designates a group capable of reacting with a free thiol radical which may include substituted 2- or 4-pyridyl group, a phenyl group or an alkoxycarbonyl group.

* * * * *

UNITED STATES PATENT AND TRADEMARK OFFICE
CERTIFICATE OF CORRECTION

PATENT NO. : 4,414,148
DATED : November 8, 1983
INVENTOR(S) : Franz K. Jansen et al It is certified that error appears in the above—identified patent and that said Letters Patent is hereby corrected as shown below:

Column 2, line 25, "functional" 2nd occurrence should read --function--
Column 5, line 30, "recin" should read --ricin--;
line 56, "conjugate chain" should read --conjugate between chain--.

Signed and Sealed this

Sixth Day of March 1984

[SEAL]

Attest:

Attesting Officer

GERALD J. MOSSINGHOFF

Commissioner of Patents and Trademarks